US012612595B1

(12) United States Patent
Liu et al.

(10) Patent No.: US 12,612,595 B1
(45) Date of Patent: Apr. 28, 2026

(54) METHOD FOR FORMING REVERSIBLE MEMBRANELESS ORGANELLE IN MICROORGANISMS

(71) Applicants: JITRI FUTURE FOOD TECHNOLOGY INSTITUTE CO., LTD., Yixing (CN); JIANGNAN UNIVERSITY, Wuxi (CN)

(72) Inventors: Long Liu, Wuxi (CN); Jian Chen, Wuxi (CN); Xueqin Lv, Wuxi (CN); Guocheng Du, Wuxi (CN); Ke Jin, Wuxi (CN); Ziyang Huang, Wuxi (CN)

(73) Assignees: JITRI FUTURE FOOD TECHNOLOGY INSITUTE CO., LTD., Yixing (CN); JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 19/006,000

(22) Filed: Dec. 30, 2024

Related U.S. Application Data

(63) Continuation of application No. PCT/CN2024/088179, filed on Apr. 17, 2024.

(30) Foreign Application Priority Data

Oct. 20, 2023    (CN) .......................... 202311365367.9

(51) Int. Cl.
| | |
|---|---|
| *A61K 38/00* | (2006.01) |
| *A61K 9/107* | (2006.01) |
| *C12N 1/18* | (2006.01) |
| *C12N 9/48* | (2006.01) |
| *C12N 15/81* | (2006.01) |
| *C12P 21/02* | (2006.01) |
| *C12Q 1/02* | (2006.01) |
| *C12Q 1/68* | (2018.01) |
| *C12R 1/865* | (2006.01) |

(52) U.S. Cl.
CPC .............. *C12N 1/18* (2013.01); *C12N 15/81* (2013.01); *C12P 21/02* (2013.01); *C12R 2001/865* (2021.05)

(58) Field of Classification Search
CPC .......... C12N 9/48; C12N 1/185; C07K 14/00; C12P 21/02; C12R 2001/865
See application file for complete search history.

(56) References Cited

U.S. PATENT DOCUMENTS

2023/0098002 A1   3/2023  Lemke et al.

FOREIGN PATENT DOCUMENTS

| CN | 117417407 A | 1/2024 |
|---|---|---|
| WO | 2020048996 A1 | 3/2020 |
| WO | 2023037356 A1 | 3/2023 |

OTHER PUBLICATIONS

Avigail Baruch Leshem et al., "Biomolecular condensates formed by designer minimalistic peptides" Nature Communications (2023) 4:421, pp. 1-9 (Jan. 26, 2023).

Benjamin S. Schuster et al., "Controllable protein phase separation and modular recruitment to form responsive membraneless organelles" Nature Communications (2018) 9:2985 (Jun. 30, 2018).

*Primary Examiner* — Maryam Monshipouri
(74) *Attorney, Agent, or Firm* — SZDC Law PC

(57) ABSTRACT

The present invention provides a method for forming a reversible membraneless organelle in microorganisms. In the present invention, in order to form a membraneless organelle in a host cell, an artificial short peptide sequence WGR-1 is fused on the basis of an intrinsically disordered protein RGG. Fusion of one WGR-1 sequence or two WGR-1 sequences connected in series can both effectively promote phase separation of RGG, thus forming a membraneless organelle in *Saccharomyces cerevisiae*, wherein the membraneless organelle RGG-(WGR-1)$_2$ has a better liquid fluidity. RGG-x-(WGR-1)$_2$ is further constructed by introducing an enzyme cleavage site x into the RGG-(WGR-1)$_2$ system in the present invention, and the reversible formation of the membraneless organelle is achieved after expression of a protease is induced. The method of the present invention has important value in customizing and controlling cell functions and the like.

2 Claims, 3 Drawing Sheets

Specification includes a Sequence Listing.

METHOD FOR FORMING REVERSIBLE MEMBRANELESS ORGANELLE IN MICROORGANISMS

This application is a Continuation Application of PCT/CN2024/088179, filed on Apr. 17, 2024, which claims priority to Chinese Patent Application No. 202311365367.9, filed on Oct. 20, 2023, which is incorporated by reference for all purposes as if fully set forth herein.

A Sequence Listing XML file named "10015_0166.xml" created on Dec. 30, 2024, and having a size of 27,557 bytes, is filed concurrently with the specification. The sequence listing contained in the XML file is part of the specification and is herein incorporated by reference in its entirety.

FIELD OF THE INVENTION

The present invention relates to a method for forming a reversible membraneless organelle in microorganisms, belonging to the field of biotechnology.

DESCRIPTION OF THE RELATED ART

Enhancing the synthesis efficiency of microbial cell factory products through organelle engineering is a commonly used synthetic biological means currently, mainly focusing on modification of endogenous organelles and construction of artificial organelles. Among them, the modification of endogenous organelles has problems, such as it is difficult for substances to cross the membrane, and it is difficult to control the metabolic network quickly and reversibly because endogenous organelles cannot be assembled or disassembled. The membraneless organelles formed by liquid-liquid phase separation based on intrinsically disordered proteins effectively avoid the above problems. Membraneless organelles with dynamic liquid fluidity can act as chemical reactors in cells, achieve limited permeation of substances, and achieve reversible phase separation of membraneless organelles by responding to chemical signals.

It is difficult for a single intrinsically disordered protein RGG to form a membraneless organelle in *Saccharomyces cerevisiae*. By expressing multiple RGGs connected in series, RGG phase separation can be promoted and a membraneless organelle can be formed in *Saccharomyces cerevisiae*. Or by expressing reported intrinsically disordered proteins such as FUSN and A-IDPs in *Saccharomyces cerevisiae* to form membraneless organelles. The intrinsically disordered proteins such as RGG (168 amino acids), FUSN (216 amino acids) and A-IDPs (175 amino acids) themselves have long sequences. Connection of multiple intrinsically disordered proteins in series repeatedly can effectively enhance their phase separation ability, but the construction process of connection them in series repeatedly is difficult because of the long length of these intrinsic proteins. Therefore, it is necessary to find a new method for modification of endogenous organelles.

SUMMARY OF THE INVENTION

In order to solve the above problems, in the present invention, the protein sequence in the process of forming a membraneless organelle is modified to enhance the phase separation effect, and a membraneless organelle with a high liquid fluidity is obtained. On this basis, a construction method of an intracellular reversible membraneless organelle is developed to achieve the reversible formation of the membraneless organelle in different host cells.

The first object of the present invention is to provide a method for forming a membraneless organelle in microorganisms, including the following steps:

introducing a protein sequence for forming the membraneless organelle into a host cell, wherein the protein sequence for forming the membraneless organelle includes an intrinsically disordered protein with an amino acid sequence as shown in SEQ ID NO: 1, and a short peptide located downstream of the intrinsically disordered protein, wherein the short peptide is a sequence as shown in SEQ ID NO: 7 or two SEQ ID NO: 7 sequences connected in series (two repeat sequences are connected directly).

Preferably, the microorganism in the present invention can be any host cell that needs to synthesize proteins in living cells, including but not limited to Enterobacterium (such as *E. coli*), yeast (such as *Saccharomyces cerevisiae*) and the like.

The second object of the present invention is to provide a method for forming a reversible membraneless organelle in microorganisms, including the following steps:

introducing a protein sequence containing an enzyme cleavage site for forming the membraneless organelle and a gene sequence encoding a cleavage enzyme into a host cell, wherein the protein sequence containing the enzyme cleavage site for forming the membraneless organelle includes an intrinsically disordered protein with an amino acid sequence as shown in SEQ ID NO: 1, a short peptide located downstream of the intrinsically disordered protein, and the enzyme cleavage site between the intrinsically disordered protein and the short peptide, wherein the short peptide is the sequence shown in SEQ ID NO: 7 or two SEQ ID NO: 7 sequences connected in series; and cleaving the enzyme cleavage site specifically by the cleavage enzyme.

Preferably, the gene sequence encoding the cleavage enzyme is regulated by a first promoter, and the protein sequence containing the enzyme cleavage site for forming the membraneless organelle is regulated by a second promoter, and the first promoter is an inducible promoter and is different from the second promoter, and the second promoter can be an inducible promoter or a constitutive promoter.

Preferably, the cleavage enzyme and the cleavage site can be arbitrarily selected as required, as long as specific cleavage can be achieved in living cells. For example, in the present invention, the TEV protease (the amino acid sequence is shown in SEQ ID NO: 5) is selected as the cleavage enzyme, and the cleavage site of the TEV enzyme is between glutamine and glycine/serine, so the sequence of the enzyme cleavage site can be SEQ ID NO: 4 or SEQ ID NO: 6.

More preferably, the protein sequence containing the enzyme cleavage site for forming the membraneless organelle is shown in SEQ ID NO: 2 or SEQ ID NO: 3. Specifically,

```
SEQ ID NO: 2: amino acid sequence of RGG-(WGR-1)₁
MESNQSNNGGSGNAALNRGGRYVPPHLRGGDGGAAAAASAGGDDRRGGAG

GGGYRRGGGNSGGGGGGGYDRGYNDNRDDRDNRGGSGGYGRDRNYEDRGY

NGGGGGGGNRGYNNNRGGGGGGYNRQDRGDGGSSNFSRGGYNNRDEGSDN

RGSGRSYNNDRRDNGGDGENLYFQGMSKGPWGRGRGRGWPGVGYGY
```

-continued

SEQ ID NO: 3: amino acid sequence of RGG-(WGR-1)$_2$
MESNQSNNGGSGNAALNRGGRYVPPHLRGGDGGAAAAASAGGDDRRGGAG

GGGYRRGGGNSGGGGGGGYDRGYNDNRDDRDNRGGSGGYGRDRNYEDRGY

NGGGGGGGNRGYNNNRGGGGGGYNRQDRGDGGSSNFSRGGYNNRDEGSDN

RGSGRSYNNDRRDNGGDGENLYFQGMSKGPWGRGRGRGWPGVGYWGRGRG

RGWPGVGYGY

The third object of the present invention is to provide a recombinant protein for constructing a membraneless organelles, including an intrinsically disordered protein with an amino acid sequence as shown in SEQ ID NO: 1, and a short peptide located downstream of the intrinsically disordered protein, wherein the short peptide is a sequence as shown in SEQ ID NO: 7 or two SEQ ID NO: 7 sequences connected in series.

The fourth object of the present invention is to provide a recombinant bacterium containing a membraneless organelle forming protein, containing the recombinant protein above.

The fifth object of the present invention is to provide a system for constructing a reversible membraneless organelle, including two parts: a protein sequence containing an enzyme cleavage site for forming a membraneless organelle and a gene sequence for coding a cleavage enzyme, wherein the protein sequence containing the enzyme cleavage site for forming the membraneless organelle includes an intrinsically disordered protein with an amino acid sequence as shown in SEQ ID NO: 1, a short peptide located downstream of the intrinsically disordered protein, and the enzyme cleavage site between the intrinsically disordered protein and the short peptide, wherein the short peptide is the sequence shown in SEQ ID NO: 7 or two SEQ ID NO: 7 sequences connected in series; and the cleavage enzyme specifically cleaves the enzyme cleavage site.

Preferably, plasmids can be used as vectors for the above two parts, respectively.

The sixth object of the present invention is to provide a recombinant bacterium containing a reversible membraneless organelle, containing the system above.

The seventh object of the present invention is to provide a method for producing a protein in living cells, including the following steps:

introducing the recombinant protein or the system above into the living cells.

Preferably, the living cells are microbial cells or animal and plant cells ex-vivo (even stem cells are commercial stem cells obtained after being approved by ethical review).

The eighth object of the present invention is to provide use of the recombinant protein, the system or the recombinant bacterium in preparing cell drugs or protein drugs. Specifically, they are used for protein customization and modification in a pharmaceutical process.

The present invention has the following beneficial effects:

(1) In the present invention, after artificial sequences WGR-1 connected in series are further expressed on the basis of an intrinsically disordered protein RGG, the phase separation ability of RGG is effectively enhanced, and finally a membraneless organelle RGG-(WGR-1)$_2$ with a high liquid fluidity is obtained. In vitro, the fluidity of RGG-(WGR-1)$_2$ is as high as 89%. Compared with existing long repeat sequences connecting a plurality of intrinsically disordered proteins in series, the membraneless organelle system of the present invention is easier to construct.

(2) RGG-x-(WGR-1)$_n$ is further constructed by introducing an enzyme cleavage site x into the membraneless organelle RGG-(WGR-1)$_2$ in the present invention, and the reversible formation of the membraneless organelle is successfully achieved after expression of a cleavage enzyme is induced, thus providing a convenient and rapid regulation strategy for the membraneless organelle.

DETAILED DESCRIPTION OF THE PREFERRED EMBODIMENTS

Figure 1:
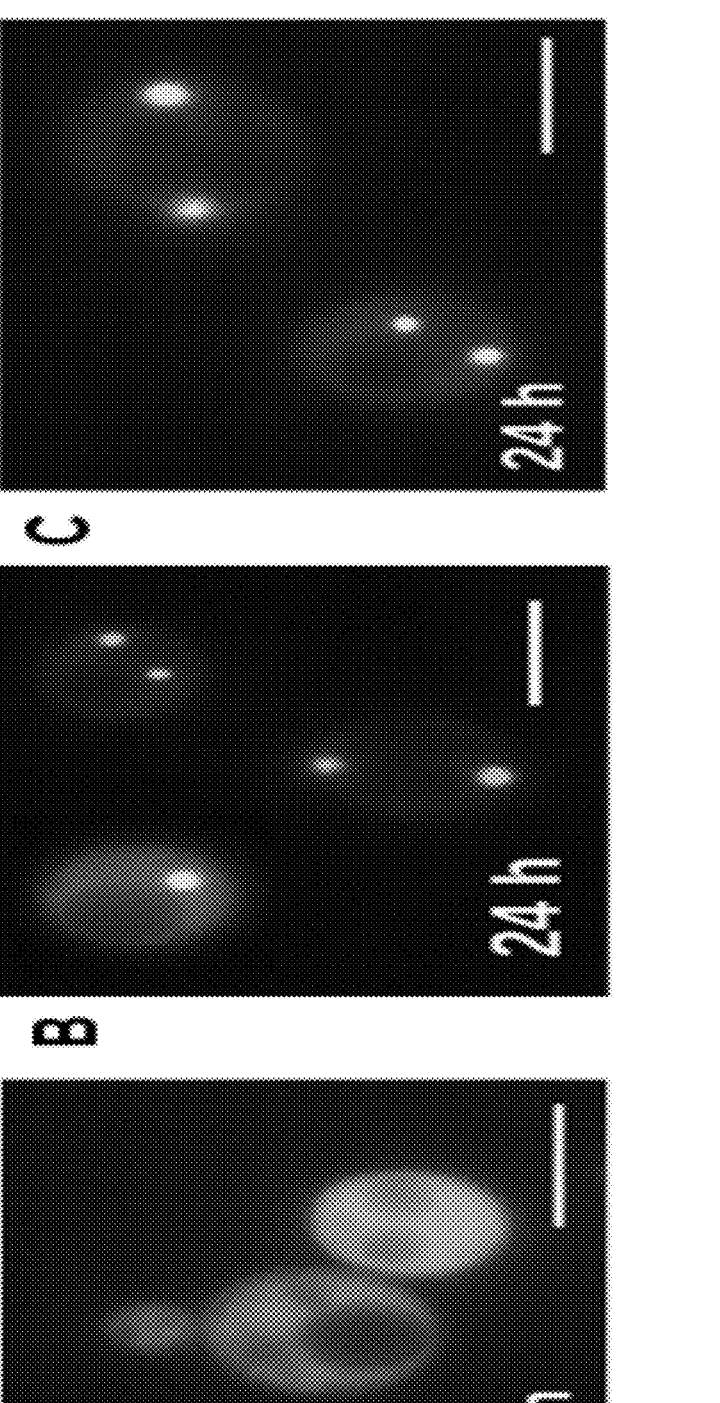
FIG. 1 is the verification result of the membraneless organelle RGG-x-(WGR-1)$_n$-EGFP in vivo.

The present invention will be further described with the attached drawings and specific examples, so that those skilled in the art can better understand and implement the present invention, but the examples given are not taken as limitations of the present invention.

The technical solutions involved in the present invention is as follows:

In the present invention, yeast was used as a starting strain, and the effect of an artificial short peptide sequence WGR-1 (SEQ ID NO: 7) with a length of only 14 amino acids on RGG phase separation was investigated, so as to construct an RGG-(WGR-1)$_n$-EGFP membraneless organelle (n represents the number of repeats);

in addition, in the present invention, a cleavage site x was introduced into the phase separation system formed by RGG-(WGR-1)$_n$-EGFP, and an RGG-x-(WGR-1)$_n$-EGFP controllable membraneless organelle system was constructed by inducing the expression of an enzyme that specifically cleaved the site x.

In the present invention, the principle of forming a reversible membraneless organelle is as follows: liquid-liquid phase separation mediated by multivalent interaction is the basis of forming a membraneless organelle. The introduction of enzyme cleavage sites of proteins can change multivalent interactions and achieve the reversible formation of membraneless organelles. Therefore, after an enzyme cleavage site and a corresponding enzyme thereof are introduced into a host cell at the same time, and before the expression of the enzyme is induced, WGR-1 can promote the phase separation of RGG, so as to form a membraneless organelle; after the expression of the enzyme is induced and the cleavage site is cleaved, the RGG protein is disconnected from the WGR-1 short peptide to destroy the phase separation system formed by RGG-(WGR-1)$_n$, and the membraneless organelle disappears. In this way, the controllable construction of the membraneless organelle can be achieved.

Example 1: Construction of Membraneless Organelle of *Saccharomyces cerevisiae* Based on Artificial Sequence RGG-x-(WGR-1)$_n$-EGFP a) Gene fragments RGG (amino acid sequence SEQ ID NO.1), RGG-x-(WGR-1) (amino acid sequence SEQ ID NO: 2) and RGG-x-(WGR-1)$_2$ (amino acid sequence SEQ ID NO: 3) were synthesized artificially, where x is an enzyme cleavage site specifically recognized by a TEV protease (amino acid sequence SEQ ID NO: 4), and the amino acid sequences 1, 2 and 3 were amplified by primers RG-F (gene sequence SEQ ID NO: 8) and RG-R (gene sequence SEQ ID NO: 9) respectively to obtain target gene fragments RG, RG1 and RG2.

b) A vector fragment pESC containing a promoter TEF1, a green fluorescent protein EGFP and a terminator CYC1 was obtained by using a plasmid pESC-TEF1-EGFP-CYC1 as a template and using primers pESC-F (gene sequence SEQ ID NO: 10) and pESC-R (gene sequence SEQ ID NO: 11) for amplification.

c) The target gene fragments RG, RG1 and RG2 were fused and expressed with pESC respectively to obtain plasmids pESC-TEF1-RGG-EGFP-CYC1, pESC-TEF1-RGG-(WGR-1)$_1$-EGFP-CYC1 and pESC-TEF1-RGG-(WGR-1)$_2$-EGFP-CYC1.

```
Primer sequence
RG-F:
                                     (SEQ ID NO: 8)
ATGGAATCAAATCAATCAAATAATGGCGGAA RG-R:
                                     (SEQ ID NO: 9)
GCTGCCGCTGCCGCTACCATAGCCGTAGCCGACTCCAG pESC-F:
                                     (SEQ ID NO: 10)
ATTATTTGATTGATTTGATTCCATGGCCGCGCTAGTTCTAGAAAACTTAG pESC-R:
                                     (SEQ ID NO: 11)
GGTAGCGGCAGCGGCAGCATGAGCAAAGGAGAAGAACTTTTCACTG
```

Figure 2:
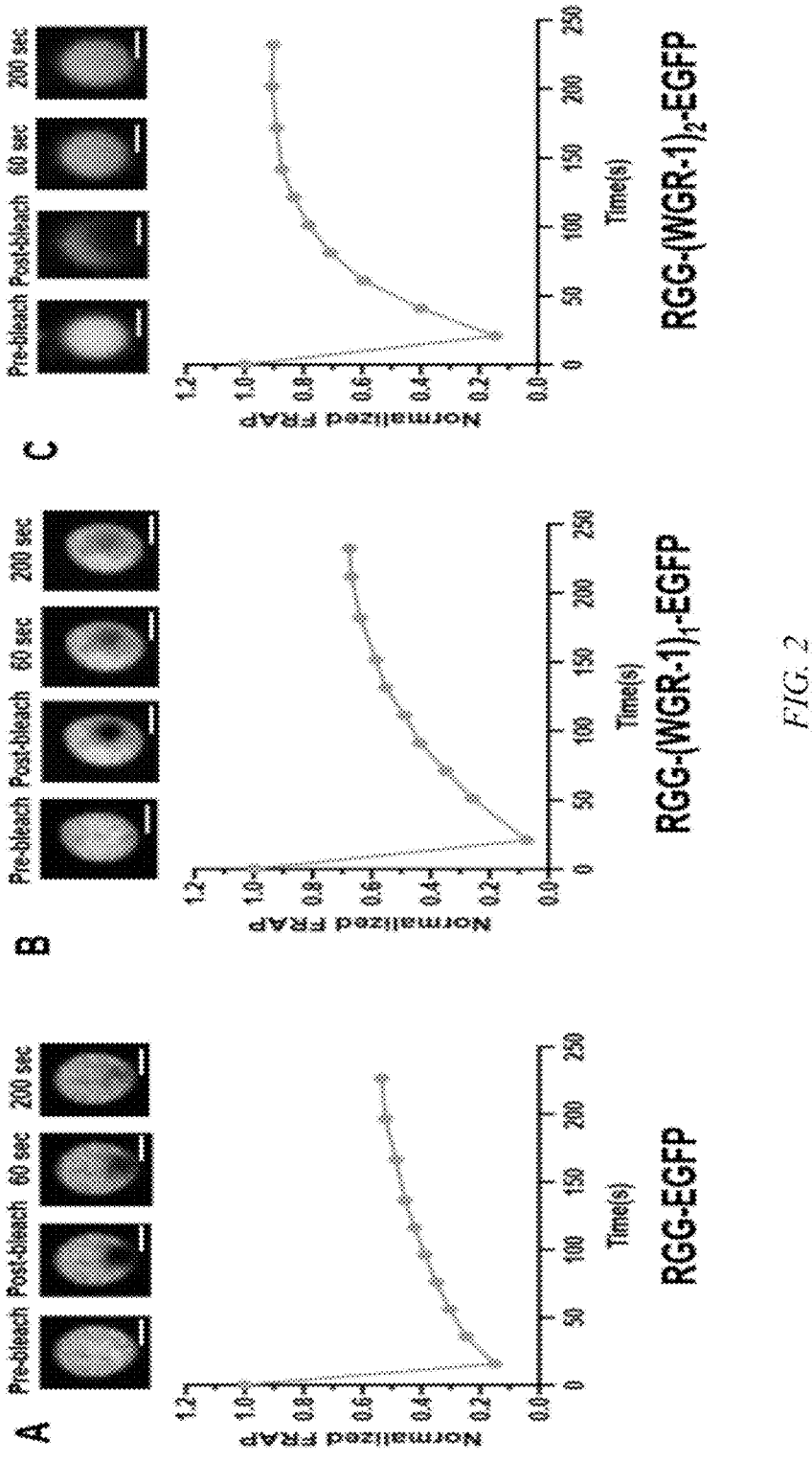
FIG. 2 is the verification result of the RGG-x-(WGR-1)$_n$-EGFP membraneless organelle in vitro.
Figure 3:
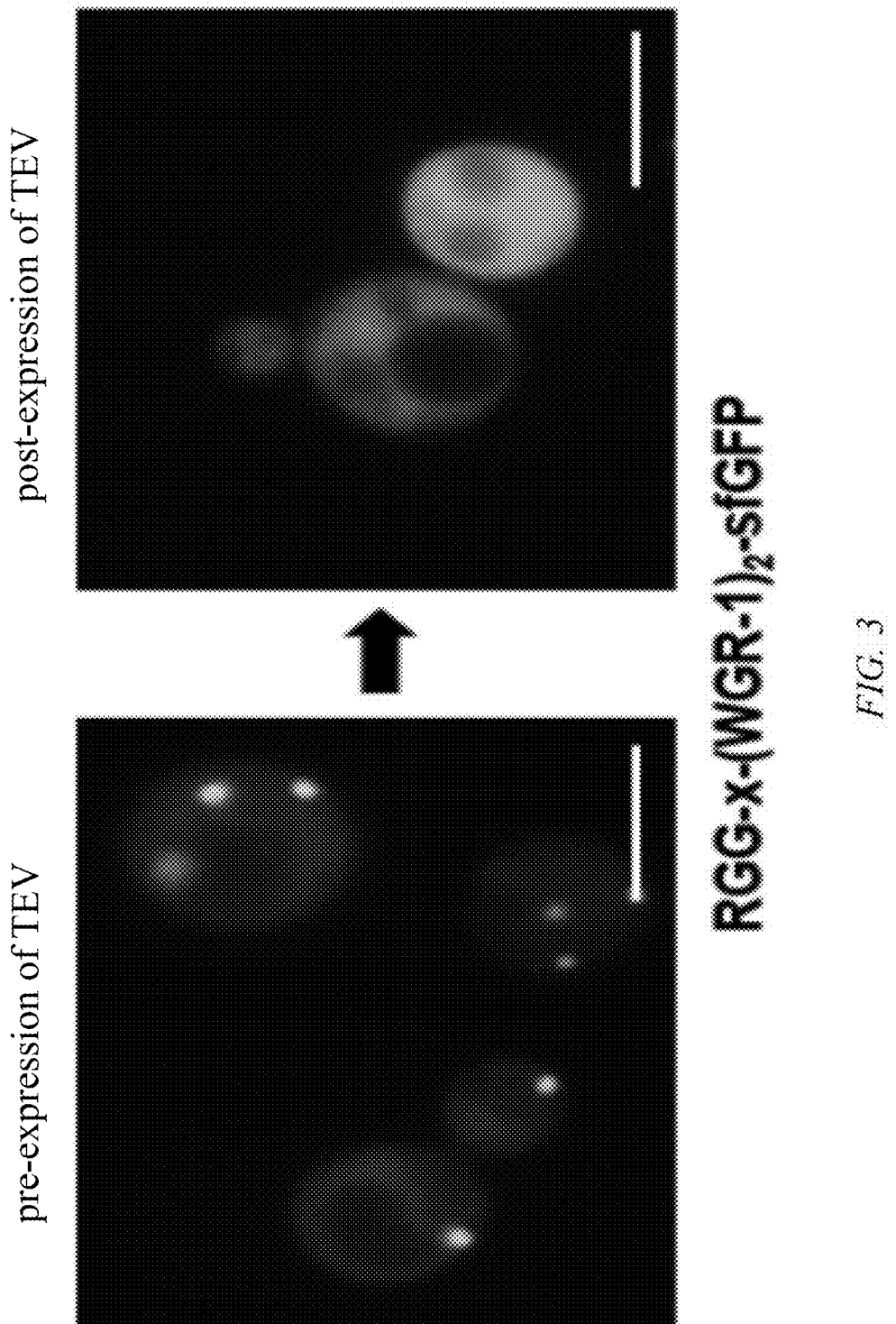
FIG. 3 is the reversible formation result of the membraneless organelle system RGG-x-(WGR-1)$_2$-EGFP induced by *Saccharomyces cerevisiae*.

Example 2: Verification of Membraneless Organelle RGG-x-(WGR-1)$_n$-EGFP In Vivo a) The plasmids pESC-TEF1-RGG-EGFP-CYC1, pESC-TEF1-RGG-(WGR-1)$_1$-EGFP-CYC1 and pESC-TEF1-RGG-(WGR-1)$_2$-EGFP-CYC1 were respectively transformed into *Saccharomyces cerevisiae* S288C, coated on G418 resistant plates and cultured at 30° C. for 2 days to obtain strains R-EGFP, RW1-EGFP and RW2-EGFP.

b) Single colonies of R-EGFP, RW1-EGFP and RW2-EGFP were picked up respectively and cultured in a 2 mL of YPD liquid medium for 24 h.

c) R-EGFP, RW1-EGFP and RW2-EGFP were observed with a fluorescence microscope. As shown in FIG. 1-A, RGG cannot form aggregates in *Saccharomyces cerevisiae*. As shown in FIGS. 1-B and 1-C, RW1-EGFP and RW2-EGFP all form spherical aggregates in cells (all the length of scales in FIG. 1-3 is 5 um).

Example 3: Verification of Membraneless Organelle Based on Artificial Sequence RGG-x-(WGR-1)$_n$-EGFP In Vitro a) Target gene fragments ER, ERG1 and ERG2 were obtained by using primers ERG-F (gene sequence SEQ ID NO: 12) and ERG-R (gene sequence SEQ ID NO: 13) to amplify the amino acid sequences 1, 2 and 3.

b) A vector fragment pET containing a promoter T7 and a 6×His tag was obtained by using a plasmid pET28a-T7-His as a template and using primers pET-F (gene sequence SEQ ID NO: 14) and pET-R (gene sequence SEQ ID NO: 15) for amplification.

c) The target gene fragments ER, ERG1 and ERG2 were fused and expressed with pET respectively to obtain plasmids pET-RGG, pET-RGG-(WGR-1)$_1$-EGFP-His and pET-RGG-(WGR-1)$_2$-EGFP-His.

d) The plasmids pET-RGG, pET-RGG-(WGR-1)$_1$-EGFP and pET-RGG-(WGR-1)$_2$-EGFP were respectively transformed into *E. coli* BL21(DE3), coated on Kana resistant plates and cultured overnight at 37° C. to obtain strains ER-EGFP-His, ERW1-EGFP-His and EWR2-EGFP-His.

e) Single colonies of ER-EGFP-His, ERW1-EGFP-His and EWR2-EGFP-His were picked up, cultured in a 2 mL of LB liquid medium for 8-10 h, and then transferred to a TB medium at 1-5%. When $OD_{600}$ was 0.6-1, IPTG was added with a final concentration of 0.5 mM, and cultured at 25° C. for 24 h.

f) The fermentation broth was purified by using a nickel column. Buffer A was 40 mM Tris-HCl (40 mM, pH7.4) with pH=7.4. Buffer B was 500 mM imidazole solution prepared from Solution A. Linear elution (0-100% Buffer B) was used to collect the target samples RGG-EGFP, RGG-(WGR-1)$_1$-EGFP and RGG-(WGR-1)$_2$-EGFP.

g) Fluorescence recovery after photobleaching can be used to analyze the fluidity of a protein condensate. The purified target sample was placed under a laser confocal microscope to carry out an experiment of fluorescence recovery after photobleaching, and the results are shown in FIG. 2. The fluorescence inside RGG-EGFP drops can be recovered to 54% of that before photobleaching (FIG. 2-A), RGG-(WGR-1)$_1$-EGFP can reach 65%, and RGG-(WGR-1)$_2$-EGFP is the highest, reaching 89%, indicating that RGG-(WGR-1)$_2$-EGFP drops have a fluidity inside the drops, and have the best fluidity.

```
ERG-F:
                                     (SEQ ID NO: 12)
ATGGAATCAAATCAATCAAATAATGGCGGAA

ERG-R:
                                     (SEQ ID NO: 13)
TACACATGGCATGGATGAGCTCTACAAACACCACCACCACCACTGA pET-F:
                                     (SEQ ID NO: 14)
CCACCACCACTGAGATCCGGCTGCTAACAAAGCC pET-R:
                                     (SEQ ID NO: 15)
TTAACTTTAAGAAGGAGATATACCATATGGAATCAAATCAATCAAAT
```

Example 4: Construction of Reversible Membraneless Organelle a) A gene fragment TEV protease (amino acid sequence SEQ ID NO: 5) was artificially synthesized and amplified by using primers TEV-F (gene sequence SEQ ID NO: 16) and TEV-R (gene sequence SEQ ID NO: 17) to obtain a target gene fragment TEV.

b) A promoter gene fragment GAL was obtained by using the genome of *Saccharomyces cerevisiae* S288C as a template, and using primers GAL1-F (gene sequence SEQ ID NO: 18) and GAL1-R (gene sequence SEQ ID NO: 19) for amplification; a terminator gene fragment CYC1 was obtained by amplification using CYC1-F (sequence SEQ ID NO: 20) and CYC1-R (sequence SEQ ID NO: 21) primers; a target gene fragment 1021b-UP was amplified by using primers UP-F (sequence SEQ ID NO: 22) and UP-R (sequence SEQ ID NO: 23); the target gene fragment 1021b-

DOWN was amplified by using primers DOWN-F (sequence SEQ ID NO: 24) and DOWN-R (sequence SEQ ID NO: 25).

c) A gene fragment LOXP-LEU was artificially synthesized and amplified by using primers LOXP-F (gene sequence SEQ ID NO: 26) and LOXP-R (gene sequence SEQ ID NO: 27) to obtain a target gene fragment LOXP.

d) The gene fragments TEV, 1021b-UP, 1021b-DOWN and LOXP were subjected to a fusion PCR by PCR, and the correct bands obtained by gel running were recovered by a column to obtain a fusion gene fragment 1021b-GAL1-TEV-CYC1.

e) The fusion gene fragment 1021b-GAL1-TEV-CYC1 was transformed into the strain RW2-EGFP obtained in Example 2, coated on an SD-His plate, and cultured at 30° C. for 2 days. The colonies were subjected to PCR with primers YZ-TEV-F (gene sequence SEQ ID NO: 28) and YZ-TEV-R (gene sequence SEQ ID NO: 29), and the resulting strain TEV-RW2-EGFP was verified.

```
TEV-F:
                                  (SEQ ID NO: 16)
GTCAAGGAGAAAAAACTATAGGTGAATCTTTATTTAAGGGTCCTCGTGAC

TA

TEV-R:
                                  (SEQ ID NO: 17)
AGTCAAGGAAGCCACTCAATTGATGAACGGGCTATTGATCATGTAATTAG

TTATGTCAC

GAL1-F:
                                  (SEQ ID NO: 18)
TGGCACTGGCCGTCGTTTTAACATGGCATTACCACCATATACATATCCAT

GAL1-R:
                                  (SEQ ID NO: 18)
AATTGTTAATATACCTCTATACTTTAACGTCAAGGAGAAAAAACTATAGG

TGAATCTTT

CYC1-F:
                                  (SEQ ID NO: 20)
ACTCAATTGATGAACGGGCTATTGATCATGTAATTAGTTATGTCACGCTT

ACATTCACG

CYC1-R:
                                  (SEQ ID NO: 21)
CGTGCGTATTATCTCTTAACTCATAATGCCGGCCGCAAATTAAAGCCTTC

G
```

-continued
```
UP-F:
                                  (SEQ ID NO: 22)
TTGGTAACAGAAGATGGCAGTATTTCCA UP-R:
                                  (SEQ ID NO: 23)
GCGTAATCATGGTCATAGCTGTTTCCTGGGAGATGCGACGAATTACTGGC LOXP-F:
                                  (SEQ ID NO: 26)
GCCAGTAATTCGTCGCATCTCCCAGGAAACAGCTATGACCATGATTACGC LOXP-R:
                                  (SEQ ID NO: 27)
ATGGATATGTATATGGTGGTAATGCCATGTTAAAACGACGGCCAGTGCCA DOWN-F:
                                  (SEQ ID NO: 24)
GAAGGCTTTAATTTGCGGCCGGCATTATGAGTTAAGAGATAATACGCACG DOWN-R:
                                  (SEQ ID NO: 25)
GAGAAAGGACTTAATCCGTACACAATGATT YZ-TEV-F:
                                  (SEQ ID NO: 28)
AACAATGGGTTTCTGGCTGGAG YZ-TEV-R:
                                  (SEQ ID NO: 29)
CCATCAATGGCTTCTAAAAGTTTTCAAAGAAGTG
```

Example 5: Induction of Reversible Formation of Membraneless Organelle System RGG-x-(WGR-1)$_2$-EGFP a) The single colony of the TEV-RW2-EGFP strain in Example 4 was picked up and cultured in a 2 mL of YPD liquid medium for 24 h. Then, as shown in FIG. 3, a membraneless organelle had been formed in the cell;

b) Galactose was added to the medium with a final concentration of 20 g/L to induce the expression of the TEV protease. After 24 h, the membraneless organelles disappeared, which reversed the phase separation of RGG-(WGR-1)$_2$, thus expanding the universality of RGG-(WGR-1)$_2$.

Obviously, the examples above are only examples for clear explanation, not limitation of the embodiments. For those of ordinary skill in the art, other changes or variations in different forms can be made on the basis of the above description. It is not necessary and impossible to exhaust all the embodiments here. The obvious changes or variations derived therefrom are still within the scope of protection created by the present invention.

---

What is claimed is:

1. A method for forming a membraneless organelle in a host cell, comprising steps of:

introducing gene fragment encoding a protein sequence containing an enzyme cleavage site for forming the membraneless organelle and a gene sequence encoding a cleavage enzyme into the host cell;

cultivating the host cell; and cleaving the enzyme cleavage site on the protein sequence specifically by the cleavage enzyme encoded by the gene sequence, wherein the protein sequence comprises SEQ ID NO: 2 or SEQ ID NO: 3.

2. The method according to claim 1, wherein the transcription of the gene sequence encoding the cleavage enzyme is initiated by a first promoter, and the transcription of the protein sequence containing the enzyme cleavage site for forming the membraneless organelle is initiated by a second promoter, and the first promoter is an inducible promoter and is different from the second promoter.

* * * * *

SEQUENCE LISTING

```
Sequence total quantity: 29
SEQ ID NO: 1          moltype = AA   length = 168
FEATURE               Location/Qualifiers
source                1..168
                      mol_type = protein
                      organism = synthetic construct
SEQUENCE: 1
MESNQSNNGG SGNAALNRGG RYVPPHLRGG DGGAAAAASA GGDDRRGGAG GGGYRRGGGN  60
SGGGGGGGYD RGYNDNRDDR DNRGGSGGYG RDRNYEDRGY NGGGGGGGNR GYNNNRGGGG  120
GGYNRQDRGD GGSSNFSRGG YNNRDEGSDN RGSGRSYNND RRDNGGDG               168

SEQ ID NO: 2          moltype = AA   length = 196
FEATURE               Location/Qualifiers
source                1..196
                      mol_type = protein
```

-continued

```
                            organism = synthetic construct
SEQUENCE: 2
MESNQSNNGG SGNAALNRGG RYVPPHLRGG DGGAAAAASA GGDDRRGGAG GGGYRRGGGN   60
SGGGGGGGYD RGYNDNRDDR DNRGGSGGYG RDRNYEDRGY NGGGGGGGNR GYNNNRGGGG   120
GGYNRQDRGD GGSSNFSRGG YNNRDEGSDN RGSGRSYNND RRDNGGDGEN LYFQGMSKGP   180
WGRGRGRGWP GVGYGY                                                  196

SEQ ID NO: 3              moltype = AA  length = 210
FEATURE                  Location/Qualifiers
source                   1..210
                         mol_type = protein
                         organism = synthetic construct
SEQUENCE: 3
MESNQSNNGG SGNAALNRGG RYVPPHLRGG DGGAAAAASA GGDDRRGGAG GGGYRRGGGN   60
SGGGGGGGYD RGYNDNRDDR DNRGGSGGYG RDRNYEDRGY NGGGGGGGNR GYNNNRGGGG   120
GGYNRQDRGD GGSSNFSRGG YNNRDEGSDN RGSGRSYNND RRDNGGDGEN LYFQGMSKGP   180
WGRGRGRGWP GVGYWGRGRG RGWPGVGYGY                                   210

SEQ ID NO: 4             moltype = AA  length = 7
FEATURE                  Location/Qualifiers
source                   1..7
                         mol_type = protein
                         organism = synthetic construct
SEQUENCE: 4
ENLYFQG                                                            7

SEQ ID NO: 5             moltype = AA  length = 236
FEATURE                  Location/Qualifiers
source                   1..236
                         mol_type = protein
                         organism = synthetic construct
SEQUENCE: 5
GESLFKGPRD YNPISSTICH LTNESDGHTT SLYGIGFGPF IITNKHLFRR NNGTLVVQSL   60
HGVFKVKNTT TLQQHLIDGR DMIIIRMPKD FPPFPQKLKF REPQREERIC LVTTNFQTKS   120
MSSMVSDTSC TFPSGDGIFW KHWIQTKDGQ CGSPLVSTRD GFIVGIHSAS NFTNTNNYFT   180
SVPKNFMELL TNQEAQQWVS GWRLNADSVL WGGHKVFMVK PEEPFQPVKE ATQLMN       236

SEQ ID NO: 6             moltype = AA  length = 7
FEATURE                  Location/Qualifiers
source                   1..7
                         mol_type = protein
                         organism = synthetic construct
SEQUENCE: 6
ENLYFQS                                                            7

SEQ ID NO: 7             moltype = AA  length = 14
FEATURE                  Location/Qualifiers
source                   1..14
                         mol_type = protein
                         organism = synthetic construct
SEQUENCE: 7
WGRGRGRGWP GVGY                                                    14

SEQ ID NO: 8             moltype = DNA  length = 31
FEATURE                  Location/Qualifiers
source                   1..31
                         mol_type = other DNA
                         organism = synthetic construct
SEQUENCE: 8
atggaatcaa atcaatcaaa taatggcgga a                                 31

SEQ ID NO: 9             moltype = DNA  length = 38
FEATURE                  Location/Qualifiers
source                   1..38
                         mol_type = other DNA
                         organism = synthetic construct
SEQUENCE: 9
gctgccgctg ccgctaccat agccgtagcc gactccag                          38

SEQ ID NO: 10            moltype = DNA  length = 50
FEATURE                  Location/Qualifiers
source                   1..50
                         mol_type = other DNA
                         organism = synthetic construct
SEQUENCE: 10
attatttgat tgatttgatt ccatggccgc gctagttcta gaaaacttag             50

SEQ ID NO: 11            moltype = DNA  length = 46
FEATURE                  Location/Qualifiers
```

-continued

```
source                    1..46
                          mol_type = other DNA
                          organism = synthetic construct
SEQUENCE: 11
ggtagcggca gcggcagcat gagcaaagga gaagaacttt tcactg                      46

SEQ ID NO: 12             moltype = DNA   length = 31
FEATURE                   Location/Qualifiers
source                    1..31
                          mol_type = other DNA
                          organism = synthetic construct
SEQUENCE: 12
atggaatcaa atcaatcaaa taatggcgga a                                       31

SEQ ID NO: 13             moltype = DNA   length = 49
FEATURE                   Location/Qualifiers
source                    1..49
                          mol_type = other DNA
                          organism = synthetic construct
SEQUENCE: 13
tacacatggc atggatgagc tctacaaaca ccaccaccac caccactga                   49

SEQ ID NO: 14             moltype = DNA   length = 34
FEATURE                   Location/Qualifiers
source                    1..34
                          mol_type = other DNA
                          organism = synthetic construct
SEQUENCE: 14
ccaccaccac tgagatccgg ctgctaacaa agcc                                    34

SEQ ID NO: 15             moltype = DNA   length = 47
FEATURE                   Location/Qualifiers
source                    1..47
                          mol_type = other DNA
                          organism = synthetic construct
SEQUENCE: 15
ttaactttaa gaaggagata taccatatgg aatcaaatca atcaaat                     47

SEQ ID NO: 16             moltype = DNA   length = 52
FEATURE                   Location/Qualifiers
source                    1..52
                          mol_type = other DNA
                          organism = synthetic construct
SEQUENCE: 16
gtcaaggaga aaaaactata ggtgaatctt tatttaaggg tcctcgtgac ta               52

SEQ ID NO: 17             moltype = DNA   length = 59
FEATURE                   Location/Qualifiers
source                    1..59
                          mol_type = other DNA
                          organism = synthetic construct
SEQUENCE: 17
agtcaaggaa gccactcaat tgatgaacgg gctattgatc atgtaattag ttatgtcac        59

SEQ ID NO: 18             moltype = DNA   length = 50
FEATURE                   Location/Qualifiers
source                    1..50
                          mol_type = other DNA
                          organism = synthetic construct
SEQUENCE: 18
tggcactggc cgtcgtttta acatggcatt accaccatat acatatccat                  50

SEQ ID NO: 19             moltype = DNA   length = 59
FEATURE                   Location/Qualifiers
source                    1..59
                          mol_type = other DNA
                          organism = synthetic construct
SEQUENCE: 19
aattgttaat atacctctat actttaacgt caaggagaaa aaactatagg tgaatcttt        59

SEQ ID NO: 20             moltype = DNA   length = 59
FEATURE                   Location/Qualifiers
source                    1..59
                          mol_type = other DNA
                          organism = synthetic construct
SEQUENCE: 20
actcaattga tgaacgggct attgatcatg taattagtta tgtcacgctt acattcacg        59

SEQ ID NO: 21             moltype = DNA   length = 51
```

-continued

```
FEATURE                  Location/Qualifiers
source                   1..51
                         mol_type = other DNA
                         organism = synthetic construct
SEQUENCE: 21
cgtgcgtatt atctcttaac tcataatgcc ggccgcaaat taaagccttc g          51

SEQ ID NO: 22            moltype = DNA   length = 28
FEATURE                  Location/Qualifiers
source                   1..28
                         mol_type = other DNA
                         organism = synthetic construct
SEQUENCE: 22
ttggtaacag aagatggcag tatttcca                                    28

SEQ ID NO: 23            moltype = DNA   length = 50
FEATURE                  Location/Qualifiers
source                   1..50
                         mol_type = other DNA
                         organism = synthetic construct
SEQUENCE: 23
gcgtaatcat ggtcatagct gtttcctggg agatgcgacg aattactggc           50

SEQ ID NO: 24            moltype = DNA   length = 50
FEATURE                  Location/Qualifiers
source                   1..50
                         mol_type = other DNA
                         organism = synthetic construct
SEQUENCE: 24
gaaggcttta atttgcggcc ggcattatga gttaagagat aatacgcacg           50

SEQ ID NO: 25            moltype = DNA   length = 30
FEATURE                  Location/Qualifiers
source                   1..30
                         mol_type = other DNA
                         organism = synthetic construct
SEQUENCE: 25
gagaaaggac ttaatccgta cacaatgatt                                  30

SEQ ID NO: 26            moltype = DNA   length = 50
FEATURE                  Location/Qualifiers
source                   1..50
                         mol_type = other DNA
                         organism = synthetic construct
SEQUENCE: 26
gccagtaatt cgtcgcatct cccaggaaac agctatgacc atgattacgc           50

SEQ ID NO: 27            moltype = DNA   length = 50
FEATURE                  Location/Qualifiers
source                   1..50
                         mol_type = other DNA
                         organism = synthetic construct
SEQUENCE: 27
atggatatgt atatggtggt aatgccatgt taaaacgacg gccagtgcca           50

SEQ ID NO: 28            moltype = DNA   length = 22
FEATURE                  Location/Qualifiers
source                   1..22
                         mol_type = other DNA
                         organism = synthetic construct
SEQUENCE: 28
aacaatgggt ttctggctgg ag                                          22

SEQ ID NO: 29            moltype = DNA   length = 34
FEATURE                  Location/Qualifiers
source                   1..34
                         mol_type = other DNA
                         organism = synthetic construct
SEQUENCE: 29
ccatcaatgg cttctaaaag ttttcaaaga agtg                             34
```